United States Patent [19]

McKendry et al.

[11] 4,208,514

[45] Jun. 17, 1980

[54] 4(3H)-OXOBENZO-2,1,3-THIADIAZINE-2,2-DIOXIDES

[75] Inventors: Lennon H. McKendry, Midland, Mich.; Walter P. Bland, Takoma Park, Md.

[73] Assignee: The Dow Chemical Company, Midland, Mich.

[21] Appl. No.: 660,576

[22] Filed: Feb. 23, 1976

[51] Int. Cl.² ............................................. C07D 285/16
[52] U.S. Cl. ............................................ 544/11; 71/91
[58] Field of Search ..................... 260/243 R; 71/91; 544/11

[56] References Cited

U.S. PATENT DOCUMENTS

| | | | |
|---|---|---|---|
| 3,708,277 | 1/1973 | Zeidler et al. | 260/243 |
| 3,822,257 | 7/1974 | Hamprecht et al. | 260/243 |
| 3,935,200 | 1/1976 | Fischer et al. | 71/91 |
| 3,997,531 | 12/1976 | Fischer et al. | 544/11 |
| 4,113,939 | 9/1978 | Fischer et al. | 544/11 |
| 4,158,559 | 6/1979 | Stubenrauch et al. | 544/11 |

FOREIGN PATENT DOCUMENTS 50-70522  6/1975  Japan .

*Primary Examiner*—John M. Ford
*Attorney, Agent, or Firm*—Edward E. Schilling; Ronald G. Brookens

[57] ABSTRACT

New derivatives of 4(3H)-oxobenzo-2,1,3-thiadiazine-2,2-dioxide and compositions and methods employing the same in the control of undesired broadleaf vegetation.

15 Claims, No Drawings

4(3H)-OXOBENZO-2,1,3-THIADIAZINE-2,2-DIOXIDES

CROSS-REFERENCE TO RELATED APPLICATON

In our copending applications Ser. Nos. 497,582 and 497,583, both filed Aug. 15, 1974, we disclose and claim 4(3H)-oxobenzo-2,1,3-thiadiazine-2,2-dioxide and -2-oxide compounds and derivatives thereof having substitution on the phenyl ring and compositions and methods of employing the same in the control of undesired vegetation. Application Ser. No. 497,582 matured into U.S. Pat. No. 3,940,389 while a division thereof, application Ser. No. 649,178, filed Jan. 15, 1976, was continued as application Ser. No. 790,520, filed Apr. 25, 1977, which was in turn continued as application Ser. No. 926,041, filed July 19, 1978 and matured into U.S. Pat. No. 4,155,746. Application Ser. No. 497,583 was continued as application Ser. No. 660,577, filed Mar. 12, 1976, and matured into U.S. Pat. No. 4,051,130 while a division of the latter application, Ser. No. 807,996, filed June 20, 1977 matured into U.S. Pat. No. 4,116,672.

BACKGROUND OF THE INVENTION

The present invention relates to certain derivatives of 4(3H)-oxobenzo-2,1,3-thiadiazine-2,2-dioxide each having various substituents on both of the thiadiazine nitrogens. This invention also relates to compositions and methods of using new derivatives of 4(3H)-oxobenzo-2,1,3-thiadiazine-2,2-dioxide as herbicides.

The prior art includes U.S. Pat. Nos. 3,041,336 and 3,217,001 which disclose certain 4 (3H)-oxobenzo-2,1,3-thiadiazine-2,2-dioxides and -2-oxides, bearing halogen, nitro or loweralkylsulfamoyl substituents on the phenyl ring which have utility as pharmacological agents. Such prior art does not disclose herbicidal utility. The use of 3-(lower alkyl)herbicides is disclosed and claimed in U.S. Pat. No. 3,708,277 and in French Pat. No. 1,538,698. It is also disclosed in German Patent Application No. P2,355,113.5 laid open May 15, 1975, that certain 1-(alkoxyalkyl)-3-alkyl-1H-2,1,3-benzothiadiazin-4(3H)-one-2,2-dioxides are useful herbicides.

An object of the present invention is to provide certain derivatives of 4(3H)-oxobenzo-2,1,3-thiadiazine-2,2-dioxide which have good herbicidal properties. Another object of the present invention is to provide a method for controlling unwanted plant growth with derivatives of 4 (3H)-oxobenzo-2,1,3-thiadiazine-2,2-dioxide and herbicidal compositions containing these compounds.

SUMMARY OF THE INVENTION

The present invention is, in one embodiment, directed to novel derivatives of 4 (3H)-oxobenzo-2,1,3-thiadiazine-2,2-dioxide corresponding to the formula:

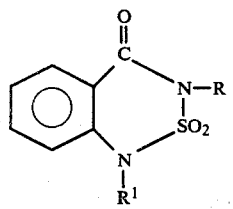

(I)

wherein:

R represents straight or branched alkyl or haloalkyl, each of 1 to 6 carbon atoms, alkenyl or haloalkenyl, each of 3 to 6 carbon atoms, alkynyl or haloalkynyl, each of 3 to 6 carbon atoms, cyanoalkyl, alkylthioalkyl or alkoxyalkyl, each of 2 to 6 carbon atoms and cycloalkyl of 3 to 6 carbon atoms;

$R^1$ represents

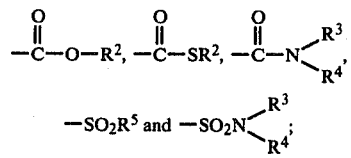

$R^2$ represents straight or branched alkyl or haloalkyl of 1 to 7 carbon atoms; alkenyl and haloalkenyl of 3 to 6 carbon atoms; cycloalkyl of 3 to 6 carbon atoms; phenyl, loweralkylphenyl and halophenyl;

$R^3$ represents alkyl of 1 to 4 carbon atoms, and cycloalkyl of 3 to 6 carbon atoms;

$R^4$ represents any of $R^3$ and alkoxy containing 1 to 4 carbon atoms, and $R^3$ and $R^4$ when taken together may constitute a 4 to 6 carbon heterocyclic radical together with the nitrogen from which each depends; and $R^5$ represents alkyl of 1 to 16 carbon atoms, haloalkyl of 1 to 4 carbon atoms, phenyl, loweralkylphenyl and halophenyl.

In a second embodiment of the present invention, any one or more of the compounds of Formula I and additional compounds, all embraced by the following Formula II, are formulated into a composition with an agricultural carrier.

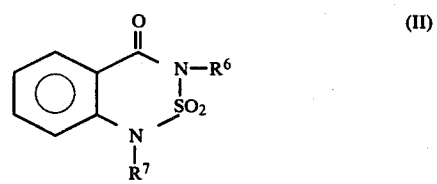

(II)

wherein:

$R^6$ represents straight or branched alkyl and halo alkyl, each of 1 to 6 carbon atoms; alkenyl and haloalkenyl, each of 3 to 6 carbon atoms; alkynyl and haloalkynyl, each of 3 to 6 carbon atoms, cyanoalkyl of 2 to 6 carbon atoms, cycloalkyl of 3 to 6 carbon atoms, alkylthioalkyl or alkoxyalkyl each of 2 to 6 carbon atoms, benzyl, phenyl, loweralkylphenyl and halophenyl;

$R^7$ represents

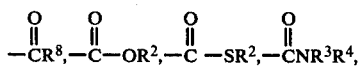

$-SO_2NR^3R^4$ and $-SO_2R^5$;

$R^2$ represents the same as indicated hereinabove;

$R^8$ represents alkyl of 1 to 11 carbon atoms, haloalkyl of 1 to 4 carbons, alkenyl, haloalkenyl, alkoxyalkyl of 1 to 4 carbons, alkenyl, haloalkenyl, alkoxyalkyl or alkylthioalkyl, each of 2 to 6 carbon atoms, cycloalkyl of 3 to 6 carbons, alkoxycarbonylalkyl of 4 to 8 carbon atoms, phenyl, loweralkylphenyl and halophenyl;

Each of $R^3$ and $R^4$ represents the same as indicated hereinabove; and $R^5$ represents the same as indicated hereinabove.

In a third embodiment of the invention compounds corresponding to Formula II are employed in methods for the control of undesired broadleaf vegetation. Such methods comprise applying a herbicidally effective amount of one or more such compounds to plants and/or their habitats.

In a further embodiment, compounds according to Formula II which have been incorporated into a herbicidal composition in the form of a wettable powder, a flowable concentrate or an emulsifiable concentrate are especially useful for the control of undesired broadleaf vegetation.

For the sake of brevity and convenience, the term "active ingredient(s)" is used hereinafter in this specification to broadly describe the novel derivatives of 4 (3H)-oxobenzo-2,1,3-thiadiazine-2,2-dioxide of Formula I as well as those compounds of Formula II employed in the method of the present invention.

DETAILED DESCRIPTION

As used in the present specification and claims, the term "herbicide" means an active ingredient which, when used in a growth controlling amount, controls or modifies the growth of undesired plants. By a "growth controlling or effective amount" is meant an amount of compound which causes a modifying effect upon the growth of plants. Such modifying effects include all deviations from natural development, for example, killing, retardation, defoliation, desiccation, regulation, stunting, tillering, and the like. By "plants" it is meant emerging seedlings and established vegetation, including the roots and above-ground portions.

The terms "loweralkyl" or "alkyl" is used herein and in the appended claims to designate a straight or branched chain alkyl or haloalkyl radical containing, where not otherwise expressly defined, from 1 to about 6 carbon atoms, such as, for example, methyl, ethyl, propyl, isopropyl, butyl, isobutyl, tert-butyl, pentyl, hexyl and the like.

The terms "halo" and "halogen", where employed herein, represent iodine, chlorine, fluorine and bromine.

The term "cycloalkyl" is employed to mean radicals containing from 3 to about 6 carbon atoms, such as, for example, cyclopropyl, cyclobutyl, cyclopentyl, cyclohexyl and the like.

The term "alkenyl" as employed in the present specification and claims designates and alkenyl radical containing from about 3 to about 6 carbon atoms, inclusive, such as, for example, propenyl, 2-methyl propenyl, butenyl, hexenyl and the like which optionally may bear one or more halogen substituents. The term "alkynyl" as used herein and in the appended claims designates an alkynyl radical of from about 3 to about 6 carbon atoms, inclusive, such as, for example, propynyl, 2-methyl propynyl, butynyl, pentynyl, hexynyl and the like which optionally may bear one or more halogen substituents.

The term "phenyl" means unsubstituted phenyl. Loweralkylphenyl as used herein means phenyl having one, two, three or more lower alkyl groups as substituents on the ring. Halophenyl as used herein means phenyl having one, two, three or more of the same or different halogens as substituents on the ring. Aryl refers to phenyl, loweralkylphenyl and halophenyl.

The active ingredients of the present invention are normally crystalline solids when substantially pure which are soluble in the usual organic solvents and somewhat insoluble in water. The active ingredients of the instant invention are generally useful as herbicides active against broadleaf plants. With respect to compounds of formula II and the use thereof herbicidal methods, compounds wherein R is selected from the group consisting of loweralkyl and haloloweralky of from two to about 4 carbon atoms are preferred. Additionally, compounds wherein $R^1$ is

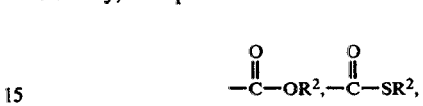

or, $-SO_2R^5$, or wherein $R^6$ is

constitute a preferred class. In all of the foregoing embodiments, compounds wherein R is isopropyl are further preferred.

The active ingredients of Formula I the instant invention can be prepared by cyclizing b-sulphamido carboxylic acid derivatives of the general formula:

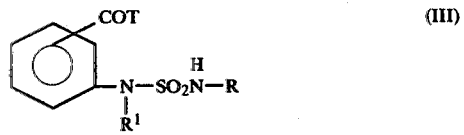

wherein R and $R^1$ are as previously defined and T is a residue which is easily split off such as, for example, a hydroxy, alkoxy or aryloxy or halo group. Also, such a compound wherein $R^1$ is hydrogen may be cyclized and then acylated to add the appropriate $R^1$ substituent.

The active ingredients of Formula II are similarly prepared using such starting materials wherein R corresponds to $R^6$ and $R^1$ corresponds to $R^7$ as previously defined.

In carrying out the preparation of the compounds of the instant invention the selected b-sulphamido carboxylic acid can be cyclized to the desired corresponding active ingredient of the instant invention with a condensing agent. Representative examples of condensing agents include, for example, phosphorous oxychloride, thionyl chloride or aqueous or alcoholic alkaline solutions such as, for example, sodium methylate and the like. The reaction can be carried out under ambient atmospheric pressures and can be conducted in the presence of inert organic solvents such as, for example, benzene, toluene, xylene, higher ethers, halogenated hydrocarbons and the like. While the reactants can be employed in stoichiometric amounts, an excess amount of the condensing agent may be employed.

The reaction is usually carried out at temperatures of from about 0° to about 150° C., and usually from about 5° about 110° C. when T is alkoxy the cyclization can be conveniently accomplished in aqueous caustic at about 10° to about 30° C. or in alcoholic alkaline solutions at reflux temperature. The product can be isolated by methods well understood in the art and appropriately selected according to whether $R^1$ is hydrogen or one of the other groups specified for $R^7$ hereinabove.

The starting materials of formula I as well as formula II can be prepared according to known methods. Procedures for preparing the same as well as literature references to the same are provided in U.S. Pat. No. 3,041,336. Starting materials wherein $R^1$ in formula III is hydrogen can, following cyclization as previously set forth, be converted to compounds where $R^1$ is other than hydrogen by reacting the same with variously substituted halides of carbonic acid, carboxylic acids, sulphonic acids; carbamic acids, sulfamic acids, and other types of selected compounds corresponding to the meaning of $R^1$ set forth hereinbefore.

Such reactions can be performed in inert organic solvents such as hydrocarbons, halogenated hydrocarbons, alkanones, the dimethyl ether of ethylene glycol, alkyl nitriles or the like and in the presence of alkali carbonates or bicarbonates.

The following examples illustrates the present invention and the manner by which it can be practiced but, as such, should not be construed as limitations upon the overall scope of the same.

EXAMPLE 1

1H-2,1,3-Benzothiadiazine-1-carboxylic Acid: 3,4-dihydro-3-(1-methylethyl)-4-oxo-, 2-Propenyl Ester, 2,2-Dioxide.

In a 500 ml 3-neck flask equipped with a magnetic stirrer, a condenser with a drying tube and a thermometer were placed 10.0 g of 3-(1-methylethyl)-1H-2,1,3-benzothiadiazin-4 (3H)-one-2,2-dioxide, 100 ml of acetonitrile and 4.94 g of potassium tertiary butoxide. The reaction mixture was heated to reflux temperature. The heat was removed, and the reaction mixture was allowed to return to room temperature (about one hour). To the flask was added dropwise a solution of 5.06 g of allyl chloroformate in 100 ml of acetonitrile during a one hour period. The mixture was stirred for 20 hours at 50°–65° C. The mixture was filtered and the acetonitrile was removed from the filtrate in vacuo. The residual dark brown crude oil was taken up in 250 ml of methylene chloride and washed with 5% $NaHCO_3$ (2×200 ml) and $H_2O$ (1×200 ml). The methylene chloride extract was dried over $Na_2SO_4$, and the methylene chloride was removed in vacuo affording 11.88 g of brown solid. The crude solid was taken up in 20 ml of methanol, stirred for one hour at room temperature, cooled and filtered affording 7.38 g of light pink solid, m.p. 70°–71.5° C.

EXAMPLES 2 and 3

Using the above described procedure, the following derivatives were prepared:

1H-2,1,3-Benzothiadiazine-1-carboxylic Acid: 3,4-Dihydro-3-(1-methylethyl)-4-oxo-, 1-Methylpropyl Ester, 2,2-Dioxide. m.p. 53.5°–55° C.
1H-2,1,3-Benzothiadiazine-1-carboxylic Acid: 3,4-Dihydro-3-(1-methylethyl)-4-oxo-, 2-Methylpropyl Ester, 2,2-Dioxide. m.p. 34°–36° C.

EXAMPLE 4

1-(2-Chloroacetyl)-3-(1-methylethyl)-1H-2,1,3-benzothiadiazin-4(3H)-one-2,2-Dioxide To 100 ml of acetonitrile was added 10.0 g of 3-(1-methylethyl)-1H-2,1,3-benzothiadiazin-4(3H)-one- -2,2-dioxide and 4.9 g of potassium t-butoxide. The mixture was stirred vigorously and 3.3 ml of chloroacetyl chloride in 50 ml acetanitrile was added dropwise over a 0.5 hour period. The resultant mixture as stirred overnight, filtered and the solvent removed from the filtrate in vacuo. The residue was washed with carbon tetrachloride and filtered. The tan granular precipitate was dissolved in 50 ml of methylene chloride and 50 ml of carbon tetrachloride was added. The methylene chloride was removed under a nitrogen atmosphere and the resultant mixture was filtered. The precipitate was washed 5% aqueous potassium carbonate, filtered and the white flocculent precipitate air dried to afford 2.23 g of 1-(2-chloroacetyl)-3-(1-methylethyl)- -1H-2,1,3-benzothiadiazin-4 (3H)-one-2,2-dioxide, m.p. 133°–135° C.

EXAMPLE 5

3-(1-Methylethyl)-1-(2,2-dimethyl-1-oxopropyl)-1H-2,1,3- -benzothiadiazin-4(3H)-one-2,2-dioxide To 100 ml of acetonitrile was added 11.6 g of the potassium salt of 3-(1-methylethyl)-1H-2,1,3-benzothiadiazin-4(3H)-one-2,2-dioxide. To the resultant stirred mixture was added dropwise 5.4 ml of trimethylacetyl chloride in 50 ml of acetonitrile over a 0.5 hour period. The resultant mixture was heated at 38°–40° C. for 22 hours, cooled, filtered and the solvent removed from the filtrate in vacuo. The residue was dissolved in 100 ml of ether and extracted with 100 ml of 5% potassium carbonate. The ether layer was washed once with 100 ml of water, dried with magnesium sulfate and filtered. The solvent was removed from the filtrate in vacuo and the solid residue, 8.3 g, extracted with 3–10 ml-portions of methanol. The resultant precipitate was air dried to afford 4.5 g of 3-(1-methylethyl)-1-(2,2-dimethyl-1-oxopropyl)-1H- -2,1,3-benzothiadiazin-4 (3H)-one-2,2-dioxide, m.p. 97.5°–99.5° C.

EXAMPLE 6

3-(1-Methylethyl)-1-(1-oxododecanyl)-1H-2,1,3-benzothiadiazin- 4 (3H)-one-2,2-dioxide Following the above procedure 10.0 g of the potassium salt of 3-(1-methylethyl)-1H-2,1,3-benzothiadiazin- -4 (3H)-one-2,2-dioxide was caused to react with 8.9 ml of lauroyl chloride at ca 25° C. After 48 hours, the mixture was filtered and the solvent removed from the filtrate in vacuo to afford 14.1 g of crude product. This was washed with two 50 ml-portions of methanol to afford upon air drying 3-(1-methylethyl)-1-(1-oxododecanyl)-1H-2,1,3-benzothiadiazin-4 (3H)-one-2,2-dioxide, m.p. 57.5°–58.5° C.

EXAMPLE 7

1H-2,1,3-Benzothiadiazin-4 (3H)-one:3-(1-methylethyl)-1-(2- -methyl-1-oxopropyl)-2,2-dioxide.

In a 500 ml, 3-necked flask equipped with a magnetic stirrer, a condenser with a drying tube, and a thermometer were placed 20.0 g of 3-(1-methylethyl)- -1H-2,1,3-benzothiadiazin-4 (3H)-one-2,2-dioxide (.083 mole), 200 ml of acetonitrile and 9.76 g of potassium tertiary butoxide (1.087 mole). The reaction was heated to reflux temperature. The heat was removed and the reaction was allowed to return to room temperature (about one hour). To the reaction was added dropwise a solution of 8.84 g of isobutyryl chloride (.083 mole) in 125 ml of acetonitrile during a two hour period. The reaction was stirred for 20 hours at room temperature.

The mixture was filtered, and the acetonitrile was removed from the filtrate in vacuo. The residual crude oil was taken up to 500 ml of methylene chloride and washed with 5% NaHCO$_3$ (2×400 ml) and H$_2$O (1×400 ml). The methylene chloride extract was dried over Na$_2$SO$_4$, and the methylene chloride was removed in vacuo affording 23.33 g of dark brown oil. The crude oil was taken up in 50 ml of methanol, stirred for 1 hour at room temperature, cooled and filtered affording 17.6 g of light pink solid, m.p. 87.5°–89° C.

EXAMPLES 8–17

Using the above general procedure, the following derivatives were prepared;

1H-2,1,3-Benzothiadiazin-4(3H)-one: 3-(1-methylethyl)-1-(2-methyl-1-oxopentyl)-; 2,2-dioxide. m.p. 45.5°–48.5° C.

1H-2,1,3-Benzothiadiazin-4(3H)-one: 1-(2-Bromo-1-oxopropyl)-3-(1-methylethyl)-; 2,2-dioxide. m.p. 112.5°–115.5° C.

1-H-2,1,3-Benzothiadiazin-4(3H)-one: 1-(cyclohexylcarbonyl)-3-(1-methylethyl)-; 2,2-dioxide. m.p. 101°–103° C.

1H-2,1,3-Benzothiadiazin-4(3H)-one: 1-(3,3-dimethyl-1-oxobutyl)-3-(1-methylethyl)-; 2,2-dioxide. m.p. 69.5°–71.5° C.

1H-2,1,3-Benzothiadiazin-4(3H)-one: 3-(1-methylethyl)-1-(1-oxo-2-butenyl)-; 2,2-dioxide. m.p. 70-20 –71.5° C.

1H-2,1,3-Benzothiadiazin-4(3H)-one: 1-benzoyl-3-(1-methyl-ethyl)-; 2,2-dioxide. m.p. 133.5°–135° C.

1H-2,1,3-Benzothiadiazin-4(3H)-one: 3-(1-methylethyl)-1-(1-oxopropyl)-; 2,2-dioxide. m.p. 96°–98° C.

1H-2,1,3-Benzothiadiazin-4(3H)-one: 1-acetyl-3-(1-methyl-ethyl)-; 2,2-dioxide. m.p. 123.5°–125.5° C.

1H-2,1,3-Benzothiadiazin-4(3H)-one: 1-methoxyacetyl-3-(1-methylethyl)-; 2,2-dioxide. m.p. 110°–112° C.

1H-2,1,3-Benzothiadiazin-4(3H)-one: 1-(2-chloro-1-oxopropyl)-3-(1-methylethyl)-; 2,2-dioxide. m.p. 85.5°–87° C.

EXAMPLE 18

1H-2,1,3-Benzothiadiazin-4(3H)-one: 3-(1-methylethyl)-1-methylsulfonyl-; 2,2-dioxide To 200 ml of acetonitrile was added with stirring 24 g(0.1 mole) of 3-(1-methylethyl)-1H-2,1,3-benzothiadiazin-4(3H)-one-2,2-dioxide and 11.8 g (0.105 mole) of potassium t-butoxide. The resultant mixture was heated to reflux, cooled, and 8.0 ml (0.105 mole of methanesulfonyl chloride in 100 ml of acetonitrile was added dropwise over a 0.5 hr period. The mixture was stirred 64 hours, filtered, and the solvent removed from the filtrate in vacuo. The crude product, 31.5 g, was washed with 2-50 ml-portions of methanol to afford 18.8 g of analytically pure 3-(1-methylethyl)-1-methylsulfonyl-1H-2,1,3-benzothiadiazin-4(3H)-one-2,2-dioxide. m.p. 156°–158° C.

EXAMPLES 19–21

Using a similar procedure, the following derivatives were prepared. In many instances the reaction was over shortly after the addition was complete. However, stirring was usually continued overnight.

1H-2,1,3-Benzothiadiazin-1-butanoic acid; γ,4-Dioxo-3-(1-methylethyl)-3,4-dihydro-, methyl ester; 2,2-dioxide. m.p. 86°–88° C.

1H-2,1,3-Benzothiadiazin-4(3H)-one: 3-(1-methylethyl)-1-propylsulfonyl-; 2,2-dioxide. m.p. 86°–88° C.

1H-2,1,3-Benzothiadiazin-4(3H)-one: 1-chloromethylsulfonyl-3-(1-methylethyl)-; 2,2-dioxide. m.p. 112°–114° C.

EXAMPLE 22

1H-2,1,3-Benzothiadiazin-1-carbothioic acid: 3,4-Dihydro-3-(1-methylethyl)-4-oxo-, S-methyl ester; 2,2-Dioxide To 200 ml of acetonitrile was added 24 g (0.1 mole) of 3-(1-methylethyl)-1H-2,1,3-benzothiadiazin-4(3H)-one-2,2-dioxide and 11.8 g of potassium t-butoxide. The mixture was heated to reflux, cooled to 50° C. and 12.6 g (0.114 mole) of methyl chlorothioformate in 100 ml of acetonitrile was added over a 0.5 hour period. The temperature was maintained at 50°–52 C. Stirring was continued at 50° C. overnight. The mixture was cooled, filtered, and the solvent removed from the filtrate in vacuo. The residual solid was washed with 3-50 ml-portions of methanol to afford 21.7 g of analytically pure S-methyl 3,4-dihydro-3-(1-methylethyl)-4-oxo-1H-2,1,3-benzothiadiazine-1-carbothioate-2,2-dioxide, m.p. 125°–127° C.

Example 23

1H-2,1,3-Benzothiadiazine-1-carbothioic acid: 3,4-Dihydro-3-(1-methylethyl)-4-oxo, S-ethyl ester; 2,2-dioxide product was recrystallized from methanol m.p. 101.5°–103.5° C.

EXAMPLE 24

1H-2,1,3-Benzothiadiazine-1-carbothioic acid: 3,4-Dihydro-3-(1-methylethyl)-4-oxo-, S-propyl ester; 2,2-dioxide was prepared in a similar manner to the above Example 22. The pure product was recovered as a yellow oil having a refractive index $R_f^{25°} = 1.5582$.

EXAMPLE 25

1H-2,1,3-Benzothiadiazin-4(3H)-one; 1-Ethylsulfonyl-3-(1-methylethyl)-; 2,2-dioxide To 200 ml of acetonitrile was added 22.1 g (0.092 mole) of 3-(1-methylethyl)-1H-2,1,3-benzothiadiazin-4(3H)-one-2,2-dioxide and 10.8 g (0.097 mole) of potassium t-butoxide. The mixture was heated to reflux, cooled to 10° C., and 9.2 ml of ethanesulfonyl chloride was added. The resultant mixture was allowed to warm to room temperature and stirring was continued overnight. The mixture was filtered and the solvent removed from the filtrate in vacuo. The residual solid was washed with 3-50 ml-portions of methanol to afford upon air drying 15.7 g of analytically pure 1-ethylsulfonyl-3-(1-methylethyl)-1H-2,1,3-benzothiadiazin-4(3H)-one-2,2-dioxide, m.p. 112°–114° C.

EXAMPLES 26–28

Using the above general procedure the following compounds were prepared:

1H-2,1,3-Benzothiadiazin-4(3H)-one: 3-(1-methylethyl)-1-(1-methylethylsulfonyl)-; 2,2-dioxide. m.p. 132°–134° C.

1H-2,1,3-Benzothiadiazin-4(3H)-one: 1-Butylsulfonyl-3-(1-methylethyl)-; 2,2-dioxide; viscous oil.

1H-2,1,3-Benzothiadiazin-4(3H)-one: 1-Hexadecylsulfonyl-3-(1-methylethyl); 2,2-dioxide; m.p. 62.5°–64° C.

EXAMPLE 29

1H-2,1,3-Benzothiadiazine-1-carboxamide: N,N-Dimethyl-3,4-dihydro-3-(1-methylethyl)-4-oxo-, 2,2-dioxide To 100 ml of toluene was added 12 g (0.05 moles) of 3-(1-methylethyl)-1H-2,1,3-benzothiadiazin-4(3H)-one-2,2-dioxide, 7.0 ml (0.05 mole) of triethylamine and 5,38 g of dimethylcarbamoyl chloride. The mixture was heated to reflux. After 3 hours an additional 0.2 ml of dimethylcarbamoyl chloride was added and after 20 hours 7 ml of triethylamine and 1 ml of dimethylcarbamoyl chloride was added. After 32 hours the mixture was cooled, filtered, and the solvent removed from the filtrate in vacuo. The residual oil crystallized from methanol at $-78°$ C. to afford upon filtration and air drying 9.30 g of analytically pure product, m.p. $82°-84.5°$ C.

EXAMPLE 30

In a similar manner 12 g of 3-(1-methylethyl)-1H-2,1,3-benzothiadiazin-4(3H)-one-2,2-dioxide was caused to react with 7.28 g of diethylcarbamoyl chloride in the presence of 14 ml of triethylamine. The crude product was crystallized from methanol to afford 12.4 g of N,N-diethyl-3,4-dihydro-3-(1-methylethyl)-4-oxo-1H-2,1,3-benzothiadiazine-1-carboxamide, m.p. $103°-104.5°$ C.

EXAMPLE 31

1H-2,1,3-Benzothiadiazin-4-(3H)-one; 1-Dimethylsulfamoyl-3-(1-methylethyl)-2,2-dioxide The above procedure was followed using benzene as the solvent. After 4 hours the refluxing solution was cooled, filtered, and the filtrate washed with 2-100 ml-portions of 5 % aqueous sodium bicarbonate and 1-100 ml-portion of $H_2O$. The organic layer was dried with $MgSO_4$, filtered, and the solvent removed in vacuo to afford 11.9 g of crude product. Recrystallization from methanol affords 8.85 g of 1-dimethylsulfamyoyl-3-(1-methylethyl)-1H-2,1,3-benzothiadiazin-4(3H)-one-2,2-dioxide, m.p. $142°-144°$ C.

In a manner similar to appropriate examples listed above, the following additional compounds were prepared having the indicated heterocyclic ring substituents:

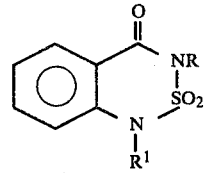

| Ex. | R | $R^1$ | MP °C. | $R_f^{25°}$ |
|---|---|---|---|---|
| 32 | i-$C_3H_7$ | —$SO_2N(C_2H_5)_2$ | 95.5–97.5 | |
| 33 | i-$C_3H_7$ | —$COCH_2OCH_2CH_3$ | 79–81 | |
| 34 | i-$C_3H_7$ | —$COCH_2CH_2OCH_2CH_3$ | | 1.5275 |
| 35 | i-$C_3H_7$ | —COS-n-$C_3H_7$ | | 1.5582 |
| 36 | i-$C_3H_7$ | —$COSC(CH_3)_3$ | 103–105 | |
| 37 | i-$C_3H_7$ | -2,4-$Cl_2$PhCO | 169.5–172 | |
| 38 | i-$C_3H_7$ | -3-Cl—PhCO | 91–92.5 | |
| 39 | i-$C_3H_7$ | —CO-n-$C_5H_{11}$ | 57–59 | |
| 40 | i-$C_3H_7$ | —CO-n-$C_4H_9$ | 39–40.5 | |
| 41 | i-$C_3H_7$ | —$CO_2$-n-$C_3H_7$ | 61–62.5 | |
| 42 | i-$C_3H_7$ | —$CO_2CH_2CH_2Cl$ | 93–95 | |
| 43 | i-$C_3H_7$ | —$CO_2$-n-$C_5H_{11}$ | 35.5–36.5 | |
| 44 | i-$C_3H_7$ | —$CO_2$-n-$C_6H_{13}$ | | 1.5180 |
| 45 | i-$C_3H_7$ | —$CO_2$Ph | 121.5–124.5 | |
| 46 | i-$C_3H_7$ | —$CO_2$-n-$C_7H_{15}$ | | 1.5195 |
| 47 | n-$C_3H_7$ | —$COCH_3$ | 81–83 | |
| 48 | n-$C_3H_7$ | —CO-n-$C_3H_7$ | 48.5–49.5 | |

In a manner similar to appropriate examples listed above, the following additional compounds were prepared having the indicated heterocyclic ring substituents:

| Ex. | R | $R^1$ | MP °C. | $R_f^{25°}$ |
|---|---|---|---|---|
| 49 | n-$C_3H_7$ | —$CO_2CH_3$ | 114–116.5 | |
| 50 | n-$C_3H_7$ | —$CO_2$-n-$C_3H_7$ | 61–62.5 | |
| 51 | n-$C_3H_7$ | —$SO_2CH_3$ | 135.5–138 | |
| 52 | n-$C_3H_7$ | —$COSC_2H_5$ | 56–57.5 | |
| 53 | $C_2H_5$ | —$CO_2CH_3$ | 110–112 | |
| 54 | $C_2H_5$ | —$CO_2$-n-$C_3H_7$ | 57–59.5 | |
| 55 | $C_2H_5$ | —$COCH_3$ | 124.5–126.5 | |
| 56 | $C_2H_5$ | —CO-n-$C_3H_7$ | 60–62.5 | |
| 57 | $C_2H_5$ | —$COSC_2H_5$ | 59.5–61.5 | |
| 58 | $C_2H_5$ | —$SO_2CH_3$ | 153–155 | |

The compounds disclosed in the present invention have been found to be suitable for use in the general post-emergent control of broadleaf weeds or other unwanted vegetation. Unexpectedly, certain of the active ingredients of the present invention have been found to be active against undesired vegetation in the presence of certain desired crop plants while producing only a negligible effect on the crop plants. For all such uses, unmodified active ingredients of the present invention can be employed. However, the present invention embraces the use of active ingredients with a material known in the art as an adjuvant in solid or liquid form. Thus, for example, an active ingredient can be dispersed on a finely divided solid and employed therein as a dust. Also, the active ingredients or a solid composition comprising the active ingredients can be dispersed in water, typically with the aid of a wetting agent, and the resulting aqueous suspension employed as a spray. In other procedures, the active ingredient can be employed as a constituent of organic liquid compositions, oil-in-water and water-in-oil emulsions, or water dispersions, with or without the addition of wetting, dispersing, or emulsifying agents.

Suitable adjuvants of the foregoing type are well known to those skilled in the art. The methods of applying the solid or liquid herbicidal formulations similarly are well known to the skilled artisan.

As organic solvents there can be employed hydrocarbons, e.g. benzene, toluene, xylene, kerosene, diesel fuel, fuel oil, and petroleum naphtha, ketones such as acetone, methyl ethyl ketone and cyclohexanone, chlorinated hydrocarbons such as carbon tetrachloride, chloroform, trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butyl Carbitol acetate and glycerine. Mixtures of water and organic solvents, either as solutions or emulsions, can be employed.

The active ingredients can also be applied as aerosols, e.g., by dispersing them in air by means of a compressed gas such as dichlorodifluoromethane or trichlorofluoromethane and other Freons and Genetrons, for example.

The active ingredients of the present invention can also be applied with adjuvants or carriers such as talc, pyrophyllite, synthetic fine silica, attapulgus clay, kieselguhr, chalk, diatomaceous earth, lime, calcium carbonate, bentonite, fuller's earth, cottonseed hulls, wheat flour, soybean flour, pumice, tripoli, wood flour, walnut shell flour, redwood flour and lignin.

As stated, it is frequently desirable to incorporate a surface active agent in the compositions of the present invention. Such surface active or wetting agents are advantageously employed in both the solid and liquid compositions. The surface active agent can be anionic, cationic or nonionic in character.

Typical classes of surface active agents include alkyl sulfonate salts, alkylaryl sulfonate salts, alkylaryl polyether alcohols, fatty acid esters of polyhydric alcohols and the alkylene oxide addition products of such esters, and addition products of long chain mercaptans and alkylene oxides. Typical examples of such surface active agents include the sodium alkylbenzene sulfonates having 10 to 18 carbon atoms in the alkyl group, alkylphenol ethylene oxide condensation products, e.g., p-isooctylphenol condensed with 10 ethylene oxide units, soaps, e.g., sodium stearate and potassium oleate, sodium salt of propylnaphthalene sulfonic acid, di(2-ethylhexyl)-ester of sodium sulfosuccinic acid, sodium lauryl sulfate, sodium decane sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat 7 and 13, sodium N-methyl-N-oleyl taurate, Turkey Red Oil, sodium dibutyl naphthalene sulfonate, sodium lignin sulfonate, polyethylene glycol stearate, sodium dodecylbenzene sulfonate, tertiary dodecyl polyethylene glycol thioether (nonionic 218), long chain ethylene oxide-propylene oxide condensation products, e.g., Pluronic 61 (molecular weight 1000), polyethylene glycol ester of tall oil acids, sodium octyl phenoxyethoxyethyl sulfate, tris(polyoxyethylene)-sorbitan monostearate (Tween 60), and sodium dihexyl sulfosuccinate.

The concentration of the active ingredients in liquid compositions generally is from about 1 to about 95 percent by weight or more, but preferably at least 5 percent. Concentrations of from about 5 to about 50 weight percent are often employed. In dusts or dry formulations, the concentration of the active ingredient can be from about 1 to about 95 weight percent or more; concentrations of from about 5 to about 50 weight percent are often conveniently employed. In compositions to be employed as concentrates, the active ingredient can be present in a concentration of from about 10 to about 98 weight percent. The active ingredient compositions can also contain other compatible additaments, for example fertilizers, phytotoxicants, plant growth regulants, pesticides and the like.

The active ingredients are most usefully brought into commerce in the form of (1) a wettable powder in which one or more of the active ingredients in finely divided form are blended with one of the wetting agents or surfactants above listed with or without combination also with a finely divided absorptive clay or other absorptive inert adjuvant or carrier as listed above; (2) a flowable concentrate which corresponds largely to a "pre-wet" wettable powder composition having as high as 50 percent solids content and containing water and-/or other appropriate liquid as well understood in the formulation art and (3) an emulsifiable concentrate in which one or more of the active ingredients are dissolved in an organic solvent, such as one of those listed, in admixture with a wetting dispersing or emulsifying agent such as those described above, whereby the concentrate will readily become an emulsion on dilution with water.

In general treating operations for the modification and control of vegetative growth plants and/or their habitats are contacted with sufficient amounts of a composition containing one or more active ingredients to provide a dosage rate of from about 0.25 to about 20 or more pounds of active ingredient per acre and more preferably about 0.5 to about 4 pounds per acre. In selective post-emergent operations in the presence of desired crop plants, the active ingredients are applied at a rate of from about 0.12 to about 2.0 pounds per acre. It is to be understood, however, that all of the active ingredients claimed and compositions containing the same may not be equally effective at similar concentrations against the same plant species. Thus, higher or lower rates than those stated may be necessary in certain instances.

So as to illustrate clearly the phytotoxic properties of the various active ingredients of the present invention, a group of controlled greenhouse experiments is described below.

Various species of plants, both broadleaf weeds and valuable crops, were planted in beds of good agricultural soil in a greenhouse. After the plants had emerged and grown to a height of about 2–6 inches, a portion of the plants were sprayed with an aqueous mixture, made by mixing a selected active ingredient and emulsifier or dispersant with water to provide solution containing 250 or 125 ppm active ingredient, employing sufficient amounts of the treating composition to provide low post emergent application rates of about 0.63 or 0.32 pounds per acre. Other portions of the plants were left untreated to serve as controls. In each test the active ingredient was a 3-methylethyl-1H-2,1,3-benzothiadiazin-4(3H)-one-2,2-dioxide having a substituent in the one position according to the invention.

After a period of 2 weeks the selective effect of the test ingredient on the plants was evaluated by a comparison with the control group of plants. The results of such operations are summarized in Table I below.

TABLE I

Selective Activity of Compounds of the Formula $$\begin{array}{c}\text{benzene ring with substituents}\\ \text{C(=O)-N(-CH(CH}_3\text{)}_2\text{)-SO}_2\text{-N(R}^1\text{ or R}^7\text{)}\end{array}$$

| Compound Having as R¹ or R⁷ | Dosage Rate lbs/Acre | % Control | | | |
|---|---|---|---|---|---|
| | | Jimson Weed | Velvet Leaf | Soybean | Cotton |
| —SO₂—⟨phenyl⟩ | 0.63 | 100 | 30 | 0 | 0 |
| | 0.32 | 100 | 0 | 0 | 0 |
| —CO₂CH₂CH₃ | 0.63 | 100 | 100 | 0 | 30 |
| | 0.32 | 100 | 70 | 0 | 10 |
| —CO₂CH₃ | 0.63 | 100 | 100 | 0 | 10 |
| | 0.32 | 100 | 100 | 0 | 0 |
| —COCH₂Cl | 0.63 | 100 | 100 | 10 | 70 |
| | 0.32 | 100 | 70 | 10 | 20 |
| —COC(CH₃)₃ | 0.63 | 100 | 100 | 0 | 40 |
| | 0.32 | 70 | 80 | 0 | 0 |

TABLE I-continued
Selective Activity of Compounds of the Formula

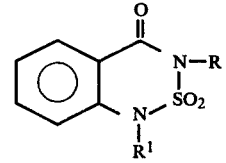

| Compound Having as $R^1$ or $R^7$ | Dosage Rate lbs/Acre | % Control Jimson Weed | Velvet Leaf | Soybean | Cotton |
|---|---|---|---|---|---|
| —CO(CH₂)₁₀CH₃ | 0.63 | 100 | 70 | 0 | 20 |
|  | 0.32 | 100 | 60 | 0 | 0 |
| —CO₂—CH—CH₂—CH₃ | 0.63 | 100 | 100 | 0 | 30 |
| \|  CH₃ | 0.32 | 100 | 100 | 0 | 30 |
| —COCHClCH₃ | 0.63 | 100 | 100 | 0 | 100 |
|  | 0.32 | 100 | 100 | 0 | 0 |
| —COSCH₂CH₃ | 0.63 | 100 | 100 | 0 | 100 |
|  | 0.32 | 100 | 100 | 0 | 100 |
| —COSCH₃ | 0.63 | 100 | 100 | 0 | 100 |
|  | 0.32 | 100 | 90 | 0 | 90 |
|  | 0.63 | 100 | 100 | 0 | 100 |
|  | 0.32 | 100 | 0 | 0 | 0 |
| —CO—⟨S⟩ |  |  |  |  |  |
| —CO—CH₂—CH₂ | 0.63 | 100 | 100 | 0 | 60 |
| \| CH₃—O—C=O | 0.32 | 100 | 70 | 0 | 0 |
|  | 0.63 | 80 | 0 | 0 | 0 |
|  | 0.32 | 80 | 0 | 0 | 0 |
| —CO—⟨Ph⟩ |  |  |  |  |  |
| —CO₂CH₂CH=CH₂ | 0.63 | 100 | 100 | 0 | 50 |
|  | 0.32 | 100 | 100 | 0 | 50 |
| —CO₂CH₂CH(CH₃)₂ | 0.63 | 100 | 100 | 10 | 0 |
|  | 0.32 | 100 | 100 | 10 | 0 |
| —SO₂N(CH₃)₂ | 0.63 | 100 | 50 | 0 | 70 |
|  | 0.32 | — | 70 | 0 | 5 |
| —CO₂CH₂CH₂Cl | 0.63 | 100 | 100 | 0 | 10 |
|  | 0.32 | 80 | 95 | 0 | 10 |
| —CON(C₂H₅)₂ | 0.63 | 100 | 20 | 0 | 90 |
|  | 0.32 | 100 | 0 | 0 | 10 |
| —CON(CH₃)₂ | 0.63 | 100 | 95 | 0 | 40 |
|  | 0.32 | 100 | 40 | 0 | — |
| —COCH=CHCH₃ | 0.63 | 100 | 100 | 0 | 0 |
|  | 0.32 | — | 70 | 0 | 0 |
| —COCH₂C(CH₃)₃ | 0.63 | 100 | 100 | 0 | 0 |
|  | 0.32 | 90 | 100 | 0 | 0 |
| —COCH₃ | 0.63 | 60 | 100 | 0 | 0 |
|  | 0.32 | 60 | 100 | 0 | 5 |
| —COC₂H₅ | 0.63 | — | 100 | 0 | 100 |
|  | 0.32 | — | 100 | 0 | 0 |
| —COCHBrCH₃ | 0.63 | 100 | 100 | 0 | 4 |
|  | 0.32 | 100 | 100 | 0 | 0 |
| —COCH₂OCH₃ | 0.63 | 100 | 100 | 0 | 0 |
|  | 0.32 | 100 | 80 | 0 | 0 |

The test results in Table I show the uniform selectivity of these compounds toward the broadleaf weeds in the presence of soybeans, and with a few exceptions, in the presence of cotton.

When a comparison test was run in a similar manner to the above post emergent tests using the comparison compound 3-methylethyl-1H-2,1,3-benzothiadiazin-4(3H)-one-2,2-dioixde at a dosage rate of about 0.32 pounds per acre, while control of velvet leaf was obtained 90 percent control of cotton was also observed. In general, at dosage rates at which velvet leaf is controlled, cotton suffers substantial damage.

In additional post emergent operations employing the above described procedure but employing a higher dosage rate of about 10 pounds per acre of active ingredient, there was demonstrated the general herbicidal activity of the present compounds and compositions against broadleaf weeds. The results are tabulated as follows in Table II.

TABLE II
General Herbicidal Activity of Compounds of the Formula at a dose rate of 10 lbs/Acre.

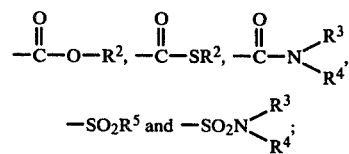

| Compound Having as $R^1$ or $R^7$ | % Control Nutsedge | Pig Weed | Annual Morning Glory | Velvet Leaf |
|---|---|---|---|---|
| —COCH(CH₃)CH₂CH₂CH₃ | 95 | — | 100 | 100 |
| —COCH(CH₃)₂ | 95 | — | 100 | 100 |
| —SO₂CH₃ | 20 | 100 | 100 | 100 |
| —SO₂CHCl | 90 | 100 | 80 | 100 |
| —CO₂CH₂CH₂CH₃ | 90 | 100 | 100 | 100 |
| —SO₂CH₂CH₃ | 85 | 100 | 100 | 100 |
| —SO₂(CH₂)₃CH₃ | 85 | 100 | 100 | 100 |
| —SO₂CH(CH₃)₂ | 85 | 100 | 100 | 100 |
| —SO₂CH₂CH₂CH₃ | 90 | 100 | 100 | 100 |
| —CO₂(CH₂)₃CH₃ | 95 | 100 | 100 | 100 |
| —COCH₂CH₂CH₃ | 90 | 100 | 100 | 100 |
| —CO₂CH(CH₃)₂ | 70 | 0 | 50 | 100 |
| —SO₂N(C₂H₅)₂ | 60 | 100 | 100 | 100 |
| —CO₂CH₂CH=CH₂ | 95 | 100 | 100 | 100 |
| —COCH₂CH₂CO₂CH₃ | 95 | — | 100 | 100 |
| —COCH=CH—CH₃ | 90 | 100 | 100 | 100 |
| —COSCH₂CH₃ | 95 | 100 | 100 | 100 |
| —COSCH₂CH₃ | 95 | 100 | 100 | 100 |
| —COSCH₃ | 85 | 100 | 100 | 100 |
| —CO₂CH₃ | 50 | 100 | 100 | 100 |
| —COCH₂Cl | 100 | 100 | 100 | 100 |
| —COCH₂OCH₃ | 90 | 100 | 100 | 100 |
| —COCHClCH₃ | 95 | 100 | 100 | 100 |
| —COCH₃ | 95 | 100 | 100 | 100 |

We Claim:
1. A compound of the formula

$$\underset{R^1}{\underset{|}{N}}\overset{\overset{O}{\|}}{C}-N-R \atop SO_2$$

wherein:
R represents straight or branched alkyl or haloalkyl, each of 1 to 6 carbon atoms, alkenyl or haloalkenyl, each 3 to 6 carbon atoms, cyanoalkyl, alkylthioalkyl or alkoxyalkyl each of 2 to 6 carbon atoms and cycloalkyl of 3 to 6 carbon atoms;
$R^1$ represents $$-\overset{O}{\underset{\|}{C}}-O-R^2, \quad -\overset{O}{\underset{\|}{C}}-SR^2, \quad -\overset{O}{\underset{\|}{C}}-N\overset{R^3}{\underset{R^4}{\diagdown}},$$

$$-SO_2R^5 \text{ and } -SO_2N\overset{R^3}{\underset{R^4}{\diagdown}};$$

$R^2$ represents straight or branched alkyl or haloalkyl each of 1 to 7 carbon atoms, alkenyl and haloalkenyl of 3 to 6 carbon atoms, cycloalkyl of 3 to 6 carbon atoms, phenyl, loweralkylphenyl and halophenyl;

R³ represents alkyl of 1 to 4 carbon atoms, and cycloalkyl of 3 to 6 carbon atoms;

R⁴ represents any of R³ and alkoxy containing 1 to 4 carbon atoms, and, R³ and R⁴ when taken together constituting a 4 to 6 carbon heterocyclic radical together with the nitrogen from which each depends; and R⁵ represents alkyl of 1 to 16 carbon atoms, haloalkyl of 1 to 4 carbon atoms, phenyl, loweralkylphenyl and halophenyl.

2. A compound as in claim 1 wherein R represents alkyl of 1 to 6 carbon atoms.

3. A compound as in claim 1 wherein R¹ is selected from the group consisting of

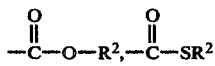

and —SO₂R⁵.

4. A compound as in claim 3 wherein R is alkyl of 1 to 6 carbon atoms.

5. A compound as in claim 3 wherein R is isopropyl.

6. A compound as in claim 1 wherein R is isopropyl.

7. 1-Methylsulfonyl-3-(1-methylethyl)-1H-2,1,3-benzothiadiazin-4(3H)-one-2,2-dioxide.

8. 1-n-Propylsulfonyl-3-(1-methylethyl)-1H-2,1,3-benzothiadiazin-4(3H)-one-2,2-dioxide.

9. 1-n-Butylsulfonyl-3-(1-methylethyl)-1H-2,1,3-benzothiadiazin-4(3H)-one-2,2-dioxide.

10. 1H-2,1,3-Benzothiadiazine-1-carboxylic acid: 3,4-dihydro-3-(1-methylethyl)-4-oxo-, methyl ester, 2,2-dioxide.

11. 1H-2,1,3-Benzothiadiazine-1-carboxylic acid: 3,4-dihydro-3-(1-methylethyl)-4-oxo-, n-propyl ester, 2,2-dioxide.

12. 1H-2,1,3-Benzothiadiazine-1-carboxylic acid: 3,4-dihydro-3-(1-methylethyl)-4-oxo-, n-butyl ester, 2,2-dioxide.

13. 1H-2,1,3-Benzothiadiazine-1-carbothioic acid: 3,4-dihydro-3-(1-methylethyl)-4-oxo-, S-methyl ester, 2,2-dioxide.

14. 1H-2,1,3-Benzothiadiazine-1-carbothioic acid: 3,4-dihydro-3-(1-methylethyl)-4-oxo-, S-n-propyl ester, 2,2-dioxide.

15. 1H-2,1,3-Benzothiadiazine-1-carbothioic acid: 3,4-dihydro-3-(1-methylethyl)-4oxo-, S-ethyl ester, 2,2-dioxide.

* * * * *

UNITED STATES PATENT AND TRADEMARK OFFICE
CERTIFICATE OF CORRECTION

PATENT NO. : 4,208,514　　　　　　　　　　　　　Page 1 of 2

DATED : June 7, 1980

INVENTOR(S) : McKendry et al.

It is certified that error appears in the above-identified patent and that said Letters Patent are hereby corrected as shown below:

| | |
|---|---|
| Column 2, Line 64 | "of 1 to 4 carbons, alkenyl, haloalkenyl, alkoxyalkyl" should be omitted. |
| Column 3, Line 51 | "designates and" should read "designates an" |
| Column 4, Line 7 | "thereof herbicidal" should read "thereof in herbicidal: |
| Column 4, Line 9 | "haloloweralky of" should read "haloloweralkyl of" |
| Column 4, Line 62 | "5° about" should read "5° to about" |
| Column 5, Line 18 | "illustrates" should read "illustrate" |
| Column 5, Line 68 | "acetanitrile" should read "acetonitrile" |
| Column 6, Line 1 | "mixture as" should read "mixture was" |
| Column 6, Line 9 | "washed 5%" should read "washed with 5%" |
| Column 6, Line 62 | "(1.087 mole)" should read "(.087) mole" |
| Column 7, Line 3 | "up to 500" should read "up in 500" |

UNITED STATES PATENT AND TRADEMARK OFFICE
CERTIFICATE OF CORRECTION

PATENT NO. : 4,208,514

DATED : June 7, 1980

INVENTOR(S) : McKendry et al.

Page 2 of 2

It is certified that error appears in the above—identified patent and that said Letters Patent is hereby corrected as shown below:

| | |
|---|---|
| Column 7, Line 14 | "prepared;" should read "prepared:" |
| Column 7, Line 22 | "1-H-2" should read "1H-2" |
| Column 7, Line 29 | "m.p. 70-20-71.5°" should read "m.p. 70°--71.5°" |
| Column 7, Line 50 | "0.105 mole of" should read "0.105 mole)of" |
| Column 8, Line 18 | "at 50°-52  C" should read "at 50°-52°C" |
| Column 14, Line 54 | "each 3 to 6" should read "each of 3 to 6" |
| Column 14, Line 54 | "atoms,cyanoalkyl," should read "atoms, alkynyl or haloalkynyl, each of 3 to 6 carbon atoms, cyanoalkyl" |
| Column 16, Line 24 | "4oxo-," should read "4-oxo-," |

Signed and Sealed this

Second Day of December 1980

[SEAL]

Attest:

SIDNEY A. DIAMOND

*Attesting Officer*    *Commissioner of Patents and Trademarks*